United States Patent

Cottle

[11] Patent Number: 5,888,227
[45] Date of Patent: Mar. 30, 1999

[54] INTER-VERTEBRAL IMPLANT

[75] Inventor: William Cottle, Vancouver, Canada

[73] Assignee: Synthes (U.S.A.), Paoli, Pa.

[21] Appl. No.: 11,011

[22] PCT Filed: Oct. 3, 1996

[86] PCT No.: PCT/CH96/00346

§ 371 Date: Feb. 2, 1998

§ 102(e) Date: Feb. 2, 1998

[87] PCT Pub. No.: WO97/15248

PCT Pub. Date: May 1, 1997

[30] Foreign Application Priority Data

Oct. 20, 1995 [WO] WIPO ............... PCT/CH95/00245

[51] Int. Cl.$^6$ ........................................... A61F 2/44
[52] U.S. Cl. ........................................................ 623/17
[58] Field of Search ............................ 623/17; 606/61

[56] References Cited

U.S. PATENT DOCUMENTS

| | | | |
|---|---|---|---|
| 5,147,402 | 9/1992 | Bohler | 623/17 |
| 5,192,327 | 3/1993 | Brantigan | 623/17 |
| 5,294,391 | 3/1994 | McMillin | 264/103 |
| 5,425,772 | 6/1995 | Brantigan | 623/17 |
| 5,522,899 | 6/1996 | Michelson | 623/17 |
| 5,658,337 | 8/1997 | Kohrs | 623/17 |
| 5,683,463 | 11/1997 | Godefroy | 623/17 |
| 5,749,916 | 5/1998 | Richelsoph | 623/17 |
| 5,766,252 | 6/1998 | Henry | 623/17 |
| 5,776,199 | 7/1998 | Michelson | 606/61 |
| 5,782,919 | 7/1998 | Zdeblick | 623/17 |

FOREIGN PATENT DOCUMENTS

| | | |
|---|---|---|
| 2151481 | 3/1995 | Canada . |
| 0307241 | 3/1989 | European Pat. Off. . |
| 0646366 | 4/1995 | European Pat. Off. . |
| WO95/08306 | 3/1995 | WIPO . |
| WO95/08964 | 4/1995 | WIPO . |
| WO95/32673 | 12/1995 | WIPO . |

Primary Examiner—Michael J. Milano
Attorney, Agent, or Firm—Pennie & Edmonds LLP

[57] ABSTRACT

An inter-vertebral implant having of a frame-like cage (1) enclosing a space (20), with a top and bottom surface (11,12), two side surfaces (13, 14), a front (16) and a rear wall (15). The top and bottom surfaces (11, 12) have a plurality of perforations (24), the total area of which amounts to 40 to 55% of the total area of said surfaces (11, 12). The individual area of a single perforation (24) is at most 20% of the total area of the top and bottom surfaces (11, 12). The ratio VH/VK between the volume VH of the space (20) and the total volume VK of the cage (1) is in the range from 70 to 90%. The cage (1) is substantially wedge-shaped with top and bottom surfaces (11, 12) diverging towards the front wall (16). This gives the advantage that, owing to the large bone bearing area of the top and bottom surfaces, the implant is prevented from sinking into the end plates of the body of the vertebra.

22 Claims, 2 Drawing Sheets

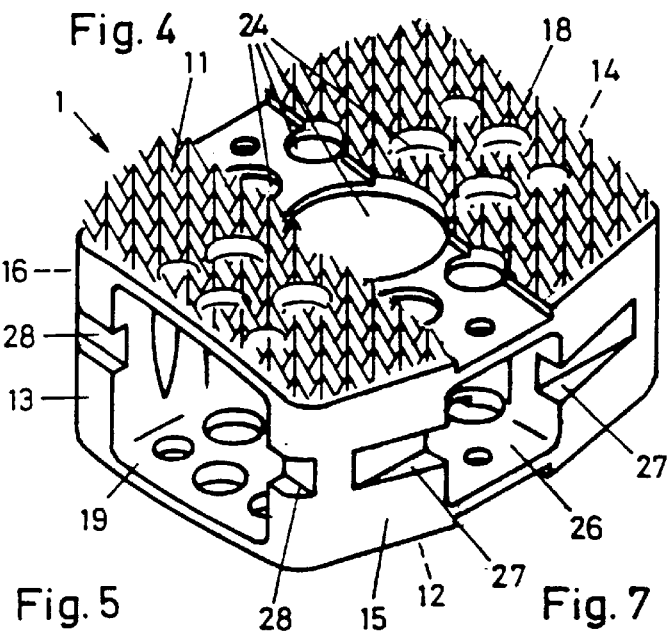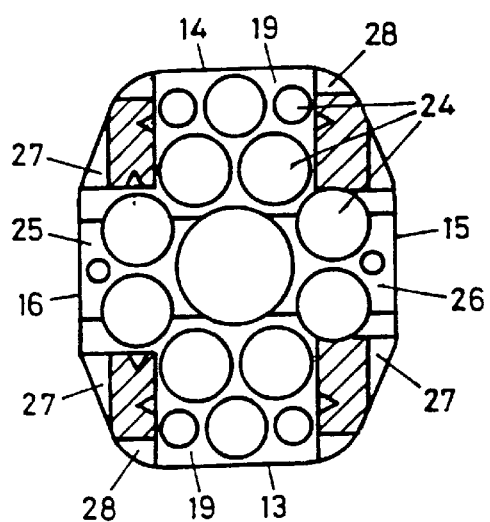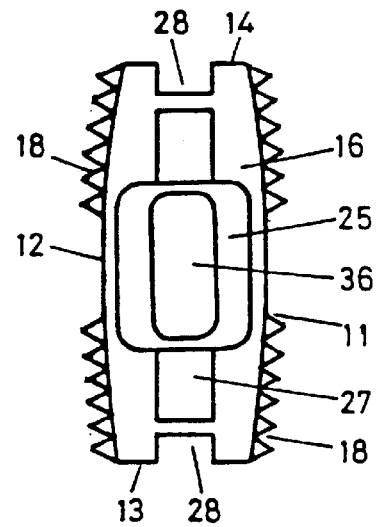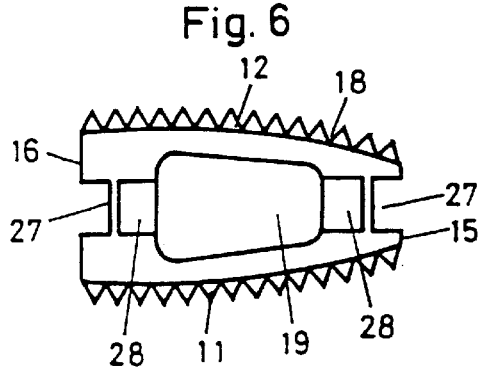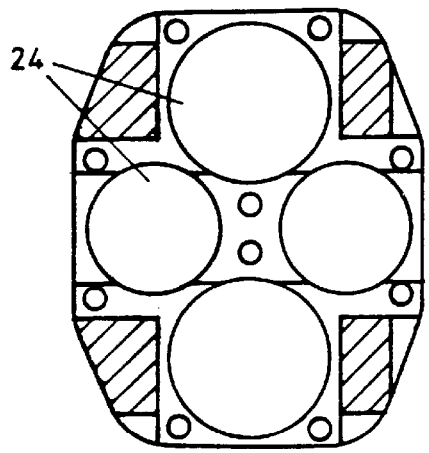

INTER-VERTEBRAL IMPLANT

TECHNICAL FIELD

The invention relates to an intervertebral implant having a frame-like cage, perforated cover and base faces, two lateral surfaces and front and rear walls, where at least one of the cover or base face has a plurality of perforations.

BACKGROUND ART

Intervertebral implants are used for the fusion of two vertebral bodies, especially in the area of the lumbar spine. One or two implants are used for each intervertebral space.

Various types of such intervertebral implants are already known from the prior art. However, all of these have the disadvantage that they harbor the risk of the implant sinking into the end plates of the affected vertebrae. For example, an intervertebral implant in the form of a ring or double ring open on top and bottom is known from the U.S. Pat. No. 5,192,327 BRANTIGAN. Since only the edge of the ring implant and at most also the narrow connection web in the case of a double ring design can act as bone contact surface, there is considerable risk that the end plates of the thereby spaced-apart vertebral bodies will sink in.

SUMMARY OF THE INVENTION

The invention is intended to remedy this. It is an object of the invention to create an intervertebral implant which can be inserted into the intervertebral space in a controlled manner, which has an optimal bone contact surface, and, due to a number of perforations in the bone contact surface, nevertheless promotes good ingrowth behavior on the part of the bone.

This object is achieved by the use of an intervertebral implant having a frame-like cage which is essentially wedge shaped, encloses a cavity and has perforated cover and base faces as bone contacting surfaces, along with two lateral surfaces, and front and rear walls. The cover and base faces diverge toward the front wall, and at least one of those faces includes a plurality of perforations whose total area makes up 40 to 55% of the total area of that face. The individual area of an individual perforation is at most 20% of the area. Also, the ratio of cavity volume to cage volume is preferably in the range of 0.11 to 0.42.

This achieves the advantage that, due to the large bone contact surface of the cover and base faces, the implant is prevented from sinking into the end plates of the vertebral bodies.

However, at the same time a number of perforations in the cover and/or base face allow the bone to grow in. The perforations in the cover and/or base face are extremely important for the bone to grow in, which causes the adjoining vertebral bodies to fuse. Surprisingly, it has appeared that the geometrical relationships of these perforations have decisive significance for clinical success. If the total area of these perforations is too small, the bone cannot grow in to the required extent so that fusion does not occur. On the other hand, if the total area of these perforations is too large, the remaining contact surface of the cover and base faces of the implants relative to the end plates of the adjoining vertebral bodies is too small, which results in excessive contact forces between the implant and the end plates, which again increases the risk that the implant will sink into the end plates.

It has appeared that the total area of the perforations in the cover and/or base face must lie in the range of 40–55% of the total area of the cover and/or base face, in order to achieve good clinical results. The total area of the perforations in the cover and/or base face preferably should be 43–51%, typically 45–49% of the total area of the cover and/or base face.

The dimensions of the individual perforations in the cover and/or base face have also proven to be very important for the degree of clinical success. If the area of the individual perforations is too small, it becomes more difficult for the bone to grow in, even though the total perforation area may be considerable. On the other hand, perforations in the cover and/or base face with too great an average area also have a negative effect, because they impair the uniform support of the end plate, thus creating a risk of the implant locally sinking into the end plate. It has appeared that the individual area of an individual perforation may amount at most to 20% of the total area of the cover and/or base face, in order to achieve good clinical results. The individual area of an individual perforation preferably should amount to 5–15%, typically 8–13% of the total area of the cover and/or base face.

The diameter of the perforations preferably should be at most 9.0 mm, typically at most 5.0 mm. The perforations affixed in the edge region of the cover and/or base face should on the average be smaller than the perforations affixed in the central region of the cover and/or base face, preferably with a gradual increase of diameter from outside to inside. The result of this is that the centrally affixed perforations permit the bone to grow in at the thinnest—and best suited—point of the end plate, while on the other hand the peripheral part of the cover and/or base face yields the best contact surface relative to the more dense edge part of the bony end plate.

Finally, it has also appeared that the geometrical relationships of the implant, which is designed as a hollow body, are important for clinical success. In order to be able to achieve good fusion of the adjoining vertebrae, it is necessary to keep the ratio VH/VK between the volume of the hollow space VH and the total volume VK of the cage in a high range of 70–90%. This guarantees that bone chips or bone replacement materials can be introduced easily, which offers the first optimal preconditions for fusion. The ratio VH/VK between the volume of the hollow space VH and the total volume VK of the cage preferably should lie in the range of 75–85%, typically 78–82%.

In a preferred embodiment, with a three-dimensional structure of the cover and base faces of the cage, high positional stability of the implant is also achieved. The three-dimensional structure can consist of teeth, longitudinal grooves, or other suitable elevations or depressions. The height of these structures should amount to 0.5–2.0 mm, preferably 1.0–1.5 mm. For example, the structure can consist of teeth, preferably in a regular arrangement.

The three-dimensional structure can be a structured hydroxyl apatite coating. It is also possible to coat the entire cage with hydroxyl apatite or with another bioactive material.

However, the three dimensional structure can also be a structural coating consisting of titanium, titanium alloys, or other physiologically compatible metals.

The cover and base faces preferably have a free edge without structurization.

In another embodiment, the cover and base faces are designed so as to bulge convex outward, so as to achieve optimal matching to the geometry of the end plates of the adjoining end plates of the vertebral bodies.

In another embodiment, the lateral faces also have perforations, whose total area should amount at most to 40% (typically at most to 30%) and at least to 15% (typically at least 20%) of the total area of the side faces. The perforations in the side faces preferably are longitudinal hole recesses.

The front wall can also have perforations, preferably in the form of longitudinal recesses.

In another embodiment, the front wall has means for receiving an instrument, by means of which the cage can be manipulated. The side faces also can have means for receiving an instrument, by means of which the cage can be manipulated.

In another embodiment of the invention, two intervertebral implants are joined to form a combination implant, with the two intervertebral implants being integrally joined to one another at their missing lateral faces. The combined front wall preferably has a longitudinal hole recess.

The inventive implant has the following advantages relative to the prior art:

a) secure against slipping;
b) improved x-ray transparency; due to the perforations in the lateral faces, as well as in the front and rear wall, the fusion behavior of the implant can easily be checked radiologically, which is greatly hindered in the case of implants according to the prior art, with closed lateral faces;
c) compressibility of bone material which may be introduced into the cage.

BRIEF DESCRIPTION OF THE DRAWINGS

The invention and further developments of the invention are explained in more detail below by means of the partially schematic representations of several embodiments.

FIG. 4 shows a view, in perspective, of a variation of an inventive implant.

FIG. 5 shows a top view of the implant of FIG. 4.

FIG. 6 shows a side view of the implant of FIG. 4.

FIG. 7 shows a view of the rear side of the implant of FIG. 4.

FIG. 8 shows a top view of a modified implant in accordance with FIG. 4.

DETAILED DESCRIPTION OF THE PREFERRED EMBODIMENTS

Figure 1:
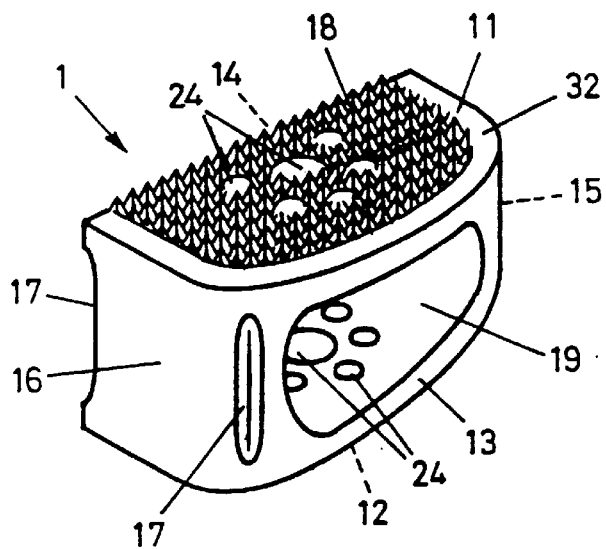
FIG. 1 shows a view, in perspective, of the inventive implant.
Figure 2:
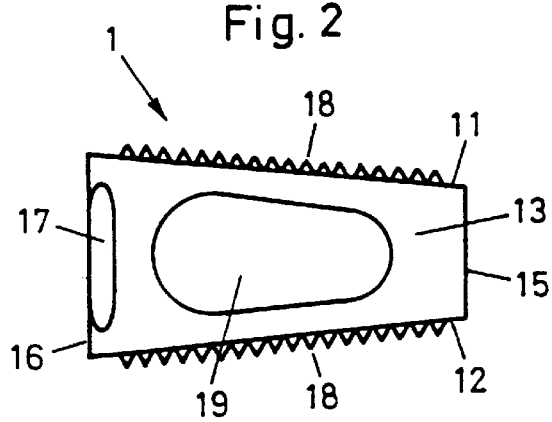
FIG. 2 shows a longitudinal section through the implant of FIG. 1.
Figure 3:
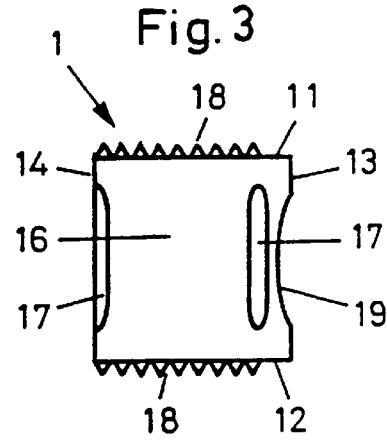
FIG. 3 shows a cross section through the implant of FIG. 1.

The intervertebral implant shown in FIGS. 1–3 essentially consists of a frame-like cage 1, closed at its cover face 11 and base face 12 (except for perforations), with two lateral faces 13 and 14, each of these having a longitudinal hole 19, a front wall 16 which has two grooves 17, and a rear wall 15. The grooves 17 serve to receive a manipulation instrument. The cage 1 is wedge-shaped, i.e. with cover and base faces 11, 12 which diverge toward the front wall 16.

In the design of FIGS. 1–3, the cover and base faces 11, 12 have a three-dimensional structure 18, preferably in the form of pointed teeth in a regular arrangement, with a height of about 1.75 mm, so as to improve the positional stability of the implant. The cover and base faces 11, 12 have a free edge 32 without such a structure 1. The free edge 32 reduces the risk of injury during and after the operation.

The cover and base faces 11, 12 have a plurality of perforations 24, whose total area amounts to 40% of the total area of the cover and base faces 11, 12. The individual area of an individual perforation 24 amounts to 15% of the total area of the cover and base faces 11, 12. The ratio VH/VK between the volume VH of the hollow space 20 and the total volume VK of the cage 1 amounts to 0.22.

As FIG. 1 shows, the front wall 16 of the cage 1 has two grooves 17 to receive an instrument, so that the cage 1 can be inserted into the intervertebral space and can be positioned there.

FIG. 4–8 show other embodiments of the invention. Apart from the modifications described below, these have the same features as the embodiment of FIGS. 1–3. The inventive implant consists of a frame-like cage 1 with a cover face 11, a base face 12, two lateral faces 13 and 14, each having a longitudinal hole 19, a front wall 16, having an aperture 25, and a rear wall 15 having an aperture 26. The aperture 25 has lateral grooves 27, which can accept a suitable manipulation instrument. The longitudinal holes 19, which are positioned in the lateral faces 13, 14, also have lateral grooves 2, which can accept a suitable manipulation instrument.

The cage 1 is wedge-shaped, i.e. with cover and base faces 11, 12 which diverge toward the front wall 16.

In the embodiment of FIGS. 4–7, the cover and base faces 11, 12 have a plurality of perforations 24. The total area of these perforations is 48% of the total area of the cover and base faces 11, 12. The individual area of an individual perforation 24 amounts to 10% of the total area of the cover and base faces 11, 12. The ratio VH/VK between the volume VH of the hollow space 20 and the total volume VK of the cage 1 amounts to 0.21.

The perforations 24 in the cover and base faces 11, 12 of the implant can be varied in many respects—within the inventive range. For example, FIG. 8 shows a variation of the perforations 24 in the cover and base faces 11, 12 of the implant of FIG. 4. Here, the total area amounts to 50% of the total area of the cover and base faces 11, 12. The individual area of an individual perforation 24 amounts to 15% of the total area of the cover and base faces 11, 12. The ratio VH/VK between the volume VH of the hollow space 20 and the total volume VK of the cage 1 is 0.22.

In all the embodiments, the cage 1 can be made of titanium, titanium alloy, ceramic, or a biocompatible plastic, e.g. polyethylene.

The clinical application will now be described in detail below.

The cage 1 shown in FIG. 1 is filled with bone chips (bone graft) or bone replacement material, possibly under compression, through the lateral perforations 19 in the form of longitudinal hole recesses. Then the filled cage 1 is pushed into the cleared intervertebral space with the help of a distending instrument. A tool, which is inserted into the two grooves 17 in the front wall 16 of the cage 1, can here be used as a manipulator.

The cage 1 can be formed either as a semi-implant, as shown in FIGS. 1–3, so that two implants must be inserted into the intervertebral space, or else it is also possible to form two semi-implants integrally, as shown in FIGS. 4–7, so that only one implant must be inserted into the intervertebral space.

What is claimed is:

1. An intervertebral implant comprising a frame-like cage which is essentially wedge-shaped, encloses a cavity, and which has perforated cover and base faces as bone-contacting surfaces, two lateral surfaces, and front and rear walls, wherein the cover and base faces diverge toward the front wall, and at least one of the cover face or base face has a plurality of perforations whose total area makes up 40 to 50% of the total area of the cover face or base face; with each individual perforation having an area amounting at most to 20% of the total area of the cover face or base face; and wherein the cavity has a volume VH, the cage has a volume VK, and the ratio of VH/VK is from 0.11 to 0.42.

2. The implant of claim 1, wherein the cover and the base faces are provided with a three-dimensional structure.

3. The implant of claim 1, wherein the cover and base faces each include a central region surrounded by an edge region, and the perforations affixed to the edge region of the cover or base face, on average, are smaller than the perforations affixed to the central region of the cover or base face.

4. The implant of claim 1, wherein the cover and base faces are configured to bulge outward.

5. The implant of claim 1, wherein the perforations have a maximum diameter of 9 mm.

6. The implant of claim 1, wherein the lateral faces have perforations whose total area is at most 40% of the total area of the lateral faces.

7. The implant of claim 6, wherein the lateral faces (13, 14) have perforations whose total area is at least 15% of the total area of the lateral faces.

8. The implant of claim 2, wherein the three-dimensional structure is a structured hydroxyl-apatite coating.

9. The implant of claim 2, wherein the three-dimensional structure is a structured coating of titanium or a titanium alloy.

10. The implant of claim 2, wherein the three-dimensional structure comprises a regular arrangement of teeth.

11. The implant of claim 2, wherein the three-dimensional structure has a height of 0.5–2.0 mm.

12. The implant of claim 1, wherein the front wall has means to receive an instrument for manipulating the cage.

13. The implant of claim 1, wherein each lateral face has means to receive an instrument for manipulating the cage.

14. The implant of claim 1, wherein the cover face and the base face each has an edge which is free of three dimensional structure.

15. The implant of claim 1, wherein the perforations in the lateral faces are longitudinal holes.

16. The implant of claim 1; wherein the front wall is equipped with perforations in the form of longitudinal holes.

17. The implant of claim 1, wherein the cage is coated with hydroxylapatite.

18. The implant of claim 1, wherein each individual perforation has an area which constitutes 5–15% of the total area of the cover or base face.

19. The implant of claim 1, wherein the ratio of VH/VK ranges between 0.17 and 0.33.

20. The implant of claim 1, wherein the total area of the perforations in the cover or base face amount to 43–51%.

21. A combination implant with two intervertebral implants in accordance with claim 1, wherein the two intervertebral implants are joined integrally together at their lateral faces.

22. The combination of implant of claim 21, wherein the combined front wall has a longitudinal hole recess.

* * * * *

UNITED STATES PATENT AND TRADEMARK OFFICE
CERTIFICATE OF CORRECTION

PATENT NO. : 5,888,227
DATED : March 30, 1999
INVENTOR(S) : William Cottle

It is certified that error appears in the above-identified patent and that said Letters Patent is hereby corrected as shown below:

Column 5, line 9, change "50" to --55--.

Signed and Sealed this

Eleventh Day of May, 1999

Attest:

Q. TODD DICKINSON

*Attesting Officer*     *Acting Commissioner of Patents and Trademarks*

UNITED STATES PATENT AND TRADEMARK OFFICE
CERTIFICATE OF CORRECTION

PATENT NO. : 5,888,227

DATED : March 30, 1999

INVENTOR : William Cottle

It is certified that error appears in the above-identified patent and that said Letters Patent is hereby corrected as shown below:

Claim 1, Column 5, line 8, please delete 50% and insert --55%--.

Signed and Sealed this

Twenty-first Day of September, 1999

Attest:

Q. TODD DICKINSON

*Attesting Officer*      *Acting Commissioner of Patents and Trademarks*